United States Patent [19]
Smidebush et al.

[11] Patent Number: 5,370,630
[45] Date of Patent: Dec. 6, 1994

[54] DEVICE FOR INJECTION OF FLUIDIC MATERIALS INTO BODY TISSUE

[76] Inventors: Michael J. Smidebush, 4232 Woodland Dr., Concord, Calif. 94521; Carl C. T. Wang, 11660 Skyline Blvd., Oakland, Calif. 94619

[21] Appl. No.: 151,420

[22] Filed: Nov. 12, 1993

[51] Int. Cl.⁵ .............................................. A61M 5/00
[52] U.S. Cl. ..................................... 604/209; 604/218
[58] Field of Search ............... 604/209, 208, 207, 187, 604/218

[56] References Cited

U.S. PATENT DOCUMENTS

| | | | |
|---|---|---|---|
| 4,659,327 | 4/1987 | Bennett et al. | 604/209 X |
| 4,865,591 | 9/1989 | Sams | 604/209 X |
| 5,017,190 | 5/1991 | Simon et al. | 604/209 X |

FOREIGN PATENT DOCUMENTS

| | | | |
|---|---|---|---|
| 12528 | 7/1903 | Austria | 604/209 |

*Primary Examiner*—John D. Yasko
*Attorney, Agent, or Firm*—Godfrey & Kahn

[57] ABSTRACT

A device (10) for injection of fluidic materials into body tissue includes a syringe (22) and an injection housing (24). The syringe (24) includes a first end (26), a second end (28), a hollow barrel (30), a plunger (32), and a rod (34) which extends through the second end (28) of the syringe (24). The housing (24) further includes a first end (42), a second end (44), and a bore (46). The first end (42) of the housing is disposed in juxtaposed relationship with the second end (28) of the syringe (22). The rod (34) extends beyond the second end (44) of the housing (24). A piston (72) travels within the bore (46) in a reciprocal fashion, and cooperates with the rod (34) in a ratchet-like fashion. The piston (72) engages the rod (34) as the piston (72) travels toward the first end (42) of the housing (24), and disengages from the rod (34) as the piston (72) travels toward the second end (44) of the housing (24). The plunger (32) of the syringe (24) is thereby advanced in increments, each of which is translatable to a specific volume of fluidic material.

15 Claims, 1 Drawing Sheet

DEVICE FOR INJECTION OF FLUIDIC MATERIALS INTO BODY TISSUE

FIELD OF THE INVENTION

The present invention relates to devices for injection of fluidic materials into body tissue and more specifically, to devices which are operable to deliver precise volumes of fluidic material to a selected injection site.

BACKGROUND OF THE INVENTION

The injection of fluidic materials into body tissue may be performed in a number of different medical procedures. In the field of ophthalmology, for example, intraocular injections may be administered for many reasons. Some of these reasons include: (1) the injection of antibodies to treat endothalmitis or prevent its onset; (2) the injection of Transforming Growth Factor Beta (TGFB) or other growth factors to treat macular disorders; (3) the injection of Tissue Plasminogen Activator (tPA) into the subretinal space to dissolve blood clots; (4) the injection of liquids and gases into the subretinal space to facilitate subretinal surgery; (5) the injection of viscoelastic substances to dissect preretinal membranes; and (6) the injection of gases into the vitreous cavity for pneumatic retinal pexy.

When intraocular injections are administered, the surgeon must control one or more of the following: injection rate, total volume administered, and location of the injected substance. The case of viscodissection is described to illustrate these requirements.

Viscodissection is a technique where preretinal membranes are hydraulically separated from the retina using a viscoelastic substance. This substance, which typically is sodium hyaluranate is injected between the membrane and the retina using a syringe and a small gage bent needle. Many surgeons find it difficult to hold the needle tip steady while they inject the fluid. As should be understood, inadvertent motion of the needle can cause damage to the retina and other surrounding tissues. Further, injecting too much fluid between the membrane and the retina, or injecting the fluid too fast, can also cause retinal damage which could lead to a retinal detachment.

A syringe adapter device which uses pneumatic energy to deliver the viscoelastic material has been previously designed. In this regard, the plunger of this previously designed device is driven by pneumatic pressure instead of finger pressure, which mitigates some of the positioning problems described above. Additionally, the pneumatic pressure source also affords good control of the volume delivered and the injection rate, providing the following factors are held constant: (1) the size of the syringe and the materials used in its construction; (2) the size, shape and material used for the plunger seal; (3) the inside diameter and inside surface finish of the injection needle; (4) the overall geometry of the injection needle; (5) the viscosity of the injected fluid and how it varies during the injection process; and (6) the temperature characteristics of the fluid and of the syringe.

A number of syringe adapters and pneumatic pressures sources are currently available, and these devices represent significant improvement over the hand-operated syringes for injecting a variety of substances. However, due to the variables listed above, these devices often cannot meet the requirements of the surgeons for precision. As will be appreciated, the volume delivered and the rate of injection are still dependent on the alertness, skill, and the responsiveness of the operator, and on the physical properties of the fluid. Accordingly, a need has arisen for a device for injection of fluidic materials into body tissue which will deliver a user-settable volume of fluid; will inject fluids at a rate precisely controlled by the operating physician; and will further minimize the risk of tissue damage that could result from a manually operated syringe.

SUMMARY OF THE INVENTION

In accordance with the present invention, a device for injection of fluidic materials includes a syringe and an injection housing. The syringe has a first end, a second end that opposes the first end, and a hollow barrel which is oriented along a longitudinal axis of the syringe. The syringe further includes a plunger which travels within the hollow barrel such that travel of the plunger toward the first end of the syringe forces the fluidic material from the hollow barrel, and travel of the plunger toward the second end draws the fluidic material into the hollow barrel. The syringe further includes a rod which is attached to the plunger and which extends beyond the second end of the syringe.

The housing has a first end, a second end that opposes the first end of the housing, and a bore which is oriented along a longitudinal axis of the housing, the first end of the housing being in juxtaposed relationship with the second end of the syringe. The longitudinal axis of the housing and the longitudinal axis of the syringe are the same such that the bore of the housing and the barrel of the syringe are in coaxial and substantial concentric relationship.

The housing further includes an end plate, a piston, a biasing means or assembly, and ratchet means. The end plate is located at the second end of the housing, and has an aperture through which the rod of the plunger extends beyond the second end of the housing. The piston travels a predetermined distance within the bore of the housing and has a hole concentric with the longitudinal axis through which the rod of the plunger extends. The biasing means or assembly is a coil spring positioned between the piston and the first end of the housing. The biasing means biases or urges the piston toward the second end of the housing. The ratchet means engages the piston with the rod of the plunger when the biasing means is overcome and the piston is urged toward the first end of the housing. The plunger is indexed toward the first end of the syringe a distance which corresponds to the predetermined distance which the piston travels. The indexed distance which the plunger travels corresponds to a precise volume of fluidic material.

A pressure chamber is formed in the bore between the piston and the end plate. The introduction of fluid into the pressure chamber provides a force to overcome the biasing means and urges the piston toward the first end of the housing. The fluid is typically compressed air. The device may further include a means for pulsing the introduction of the fluid into the pressure chamber, each pulse indexing the plunger toward the first end of the syringe a given distance which the piston travels. The volume of fluidic material forced from the hollow barrel thereby corresponds to the number of pulses produced by the pulsing means.

The device of the present invention affords good control of the volume and injection rate, notwithstanding the aforementioned variables related to the syringe, the viscosity and temperature of the fluid, and operator skill.

Further objects, features, and advantages of the invention will be apparent from the following detailed description taken in conjunction with the accompanying drawings.

DETAILED DESCRIPTION OF THE PREFERRED EMBODIMENT

Figure 1:
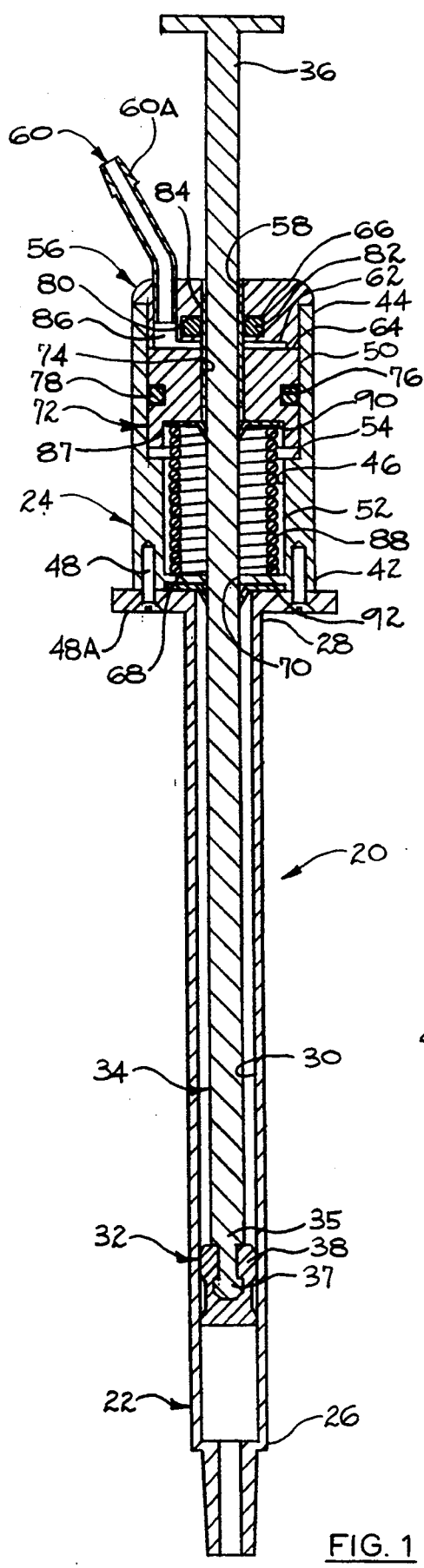
FIG. 1 is a longitudinal cross-sectional view taken through the injection handpiece of the device for injection of fluidic materials into body tissue of the present invention.
Figure 4:
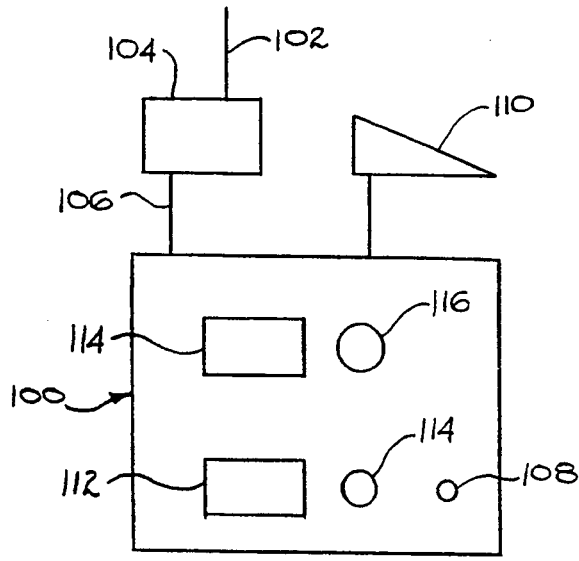
FIG. 4 is a plan view of the pneumatic power control console of the device for injection of fluidic materials into body tissue of the present invention.
Figure 2:
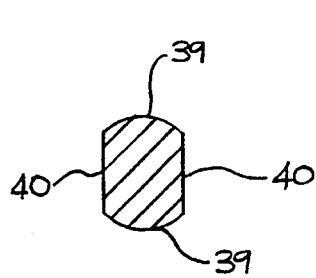
FIG. 2 is a horizontal cross-sectional view taken through the rod which is attached to the plunger of the device for injection of fluidic materials into body tissue of the present invention.
Figure 3:
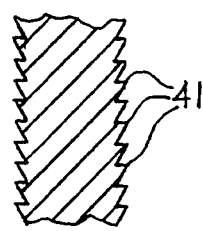
FIG. 3 is a vertical cross-sectional view taken through the rod which is attached to the plunger of the device for injection of fluidic materials into body tissue of the present invention.

With reference to the drawings, the device for injection of fluidic materials is shown generally at numeral 20. The device 20 includes a syringe 22 and an injection housing 24. The syringe 22 is similar to a standard syringe used to inject fluids and has a first end 26, a second end 28 that opposes the first end 26, and a hollow barrel 30 which is oriented along a longitudinal axis of the syringe 22. The syringe 22 includes a plunger 32 which travels within the hollow barrel 30 such that travel of the plunger 32 toward the first end 26 forces the fluidic material from the hollow barrel 30 and travel of the plunger 32 toward the second end 28 draws the fluidic material into the hollow barrel 30. The syringe 22 further includes a rod 34 which is attached to the plunger 32 at the distal end 35 of the rod 34. The rod 34 has a length which is oriented along the longitudinal axis of the syringe 22 and extends beyond the second end of the syringe 22 at the proximal end 36 of the rod 34. The rod 34 is attached to the plunger 32 at the distal end by having a male portion 37 of the rod 34 fit within a female portion 38 of the plunger 32. FIG. 2 shows a horizontal section through the rod 34, the rod 34 having two curved faces 39 and two flat faces 40 along its length. FIG. 3 shows a vertical section through the rod 34, the curved faces 36 having axially oriented teeth 41 along its length.

The injector housing 24 has a first end 42; a second end 44 that opposes the first end 42 of the housing 24; and a bore 46 which is oriented along a longitudinal axis of the housing 24, the first end 42 of the housing 24 being attached to the second end 28 of the syringe 22 by fasteners 48 which extend through flanges 48A at the second end of the syringe 22 and into the first end 42 of the injector housing 24. The injector housing 24 is attached to the syringe 22 such that the longitudinal axis of the housing 24 and the longitudinal axis of the syringe are coaxially aligned and the bore 46 of the housing 24 and the barrel 30 of the syringe 22 are in substantially concentric relationship.

The bore 46 of the housing 24 has a region 50 having a first diametral dimension; a region 52 having a second diametral dimension which is less than the first diametral dimension; and a ledge 54 formed at the interface between the first region 50 and the second region 52. The injector housing 24 further has an end plate 56 located at the second end 44 of the housing 24. The end plate 56 has an aperture 58 through which the rod 34 of the plunger 32 extends beyond the second end 44 of the housing 24. The end plate 56 further includes a port 60 through which a fluid, such as, for example, compressed air, may be introduced into the bore 46. The port 60 terminates in a barbed fitting 60A which acts as a pneumatic connection. The end plate 56 sealingly and matingly fits against the second end 44 of the housing 24 and the portion of the end plate 56 facing the bore 46 is stepped, having a first step 62 in the region about the aperture 58, and a second step 66. The housing 24 is also closed at the first end 42 by a wall 68 which is integral with the housing 24 and which abuts against the flanges at the second end 28 of the syringe 22. Like the end plate 56, the wall 68 has an aperture 70 through which the rod 34 of the plunger 32 passes.

A piston 72 is located within the bore 46 in the region 50. The piston 72 is capable of travel between the third step 64 of the end plate 56 and the ledge 54 formed at the interface between the region 50 and the region 52. The piston 72 is thus capable of travelling a predetermined distance within the housing 24 between the third step 64 and the ledge 54. The piston 72 has a hole 74 which is coaxially aligned with the longitudinal axis and through which the rod 34 of the plunger 32 extends. The piston 72 has a recess 76 which extends about the circumference of the piston 72 into which an O-ring seal 78 is nested, thereby sealing the interface between the piston 72 and the bore 46. The end plate 56 has a recess 80 which extends about the aperture 58 into which an O-ring seal 82 is nested, thereby sealing the interface between the sleeve 84 and the end plate 56. A cylindrical sleeve 84 is firmly pressed or friction fit into the hole 74 of the piston 72, the rod 34 passing through the sleeve 84. A pressure chamber 86 is thereby formed in the bore 46 between the piston 72 and the end plate 56, the pressure chamber 86 being sealed by the O-ring seal 78, the O-ring seal 82, and the sleeve 84.

The side of the piston 72 which faces the first end 42 of the housing 24 has a recessed surface 87. A coil spring 88 is positioned between the piston 72 and the first end 42 of the housing 24 and operates as a biasing means or assembly. The spring 88 is nested at one end within the recessed surface 87 and abuts at the other end against the wall 68. The coil spring 88 is oriented such that the windings are concentric with the longitudinal axis through which the rod of the plunger extends. The spring 88 biases the piston toward the second end 44 of the housing and against the third step 64 of the end plate 56 unless the piston 72 is subject to a force in the direction of the first end 42 of the housing 24 such that the biasing force of the spring 88 is overcome and the piston 72 is urged toward the first end 42 of the housing 24.

The device 20 further includes leaf spring washers 90 and 92. The leaf spring washer 90 is located intermediate the piston 72 and the spring 88, and the leaf spring washer 92 is located intermediate the second end 28 of the syringe 22 and the injection housing 24. The washers 90 and 92 have axially oriented holes through which the rod 34 of the plunger 32 passes. The leaf spring washers 90 and 92, in combination with the teeth 40 of the rod 34, form a ratchet assembly such that the leaf spring washers 90 and 92 engage the teeth 40 of the rod 34 when the piston 72 is urged toward the first end 42 of the housing 24. The rod 34 and the plunger 32 are thus moved or indexed toward the first end 26 of the syringe 22 simultaneously with the piston 72. The indexing of the plunger 32 toward the first end 26 is of a distance which corresponds to the predetermined distance which the piston 72 travels, that is, the distance between the end points formed by the third step 64 of the end plate 56 and the ledge 54. As should be understood, the movement of the piston 72 a set, or known, distance corresponds to a set distance which the plunger 32 travels. In a hollow barrel 30 of uniform crosssection, the distance that the plunger 32 travels will directly correspond with a set volume of fluid which is forced from the first end 26 of the syringe 22. Upon relaxation of the force which is urging the piston 72 toward the first end 42 of the housing 24, the ratchet assembly formed by the leaf spring washers 90 and 92 will release engagement and the piston 72 will move toward the second end 28 of the housing 24 and return to a position where the piston 72 abuts against the second step 66 of the end plate 56. Because of the engagement of the ratchet assembly only when the piston moves toward the first end 42 of the housing (and toward the first end 26 of the housing), upon successive cycles of application and relaxation of force the piston 72 reciprocates back and fourth between the second step 64 and the ledge 54. As a result, the plunger 32 will only advance or index in set increments toward the first end 26 of the syringe 22.

In the operation of the device 20, a gas originating from a pneumatic source is introduced into the pressure chamber 86 through the port 60. In response, the piston 72 is urged toward the first end 42 of the housing 24 by the force exerted by the gas under pressure, the force being sufficient to overcome the biasing force of the coil spring 88. The leaf spring 90 the piston 72 thereby moving in unison to deliver a precise volume of fluid, as described above. The gas is then permitted to exit through the port 60, thereby permitting the spring 88 to push the piston 72 and the leaf spring 90 toward the end plate 56. As should be understood, the plunger 32 is prevented from moving toward the second end 28 of the syringe 22 when the leaf spring 92 engages one of the teeth 41 on the rod 34. In continuous operation, a series of pressure pulses are delivered to the pressure chamber 86 such that the plunger 32 is advanced or indexed toward the first end 26 of the syringe 22 in a precise increment for each pulse, and further such that the indexed distance which the plunger 32 travels corresponds to a precise volume of fluidic material.

The device 20 may further incorporate a pneumatic power control console 100, which is shown in schematic form in FIG. 5. In the use of the power control console 100, electric power is supplied via a cable 102 to a compressor 104 which generates pneumatic power and supplies such pneumatic power to the control console 100 through a conduit 106. The control console 100 forms pressure pulses frown the pneumatic power supplied through the conduit 106 and delivers them to a connector 108 at a rate controlled by a foot pedal 110. A display 112 is a counter which shows the actual number of pulses delivered to the connector 108. A pushbutton 114 may be employed to reset the counter 112 to zero. The control console 100 may also have a setting at a display 114 which may be set by a knob 116 to provide an upper limit to the number of pulses, and the volume of fluidic material, which is to be administered. The design of a circuit which accomplishes the above controls is within the ambit of one skilled in the art.

In the operation of the control console 100, the operator sets the display 114 by the knob 116 or similar control to adjust the "maximum number" of pulses setting shown on the display 114. Pressure pulses are delivered to the connector 108 at a rate controlled by the foot pedal 108 and are counted on the display 112. The delivery of pressure pulses stops when the foot pedal 110 is released, or stops automatically when the actual number of pulses on the display 112 equals the maximum number of pulses which has been set on the display 114.

It is to be understood that the invention is not confined to the particular construction and arrangement of parts herein illustrated and described, but embraces such modified forms thereof as come within the scope of the following claims.

What is claimed is:

1. A device for injection of fluidic materials into body tissue, the device comprising:
   (a) a syringe having a first end, a second end that opposes the first end, and a hollow barrel which is oriented along a longitudinal axis of the syringe, the syringe including a plunger which travels within the hollow barrel such that travel of the plunger toward the first end forces the fluidic material from the hollow barrel and travel of the plunger toward the second end draws the fluidic material into the hollow barrel, and the syringe further including a rod which is attached to the plunger and which extends beyond the second end of the syringe;
   (b) a housing having a first end, a second end that opposes the first end of the housing, and a bore which is oriented along a longitudinal axis of the housing, the first end of the housing being in juxtaposed relationship with the second end of the syringe, and wherein the longitudinal axis of the housing and the longitudinal axis of the syringe are the same such that the bore of the housing and the barrel of the syringe are in concentric relationship, the housing further comprising:
      (i) an end plate which is located at the second end of the housing, the end plate having an aperture through which the rod of the plunger extends beyond the second end of the housing;
      (ii) a piston which travels a predetermined distance within the bore of the housing, the piston having a hole concentric with the longitudinal axis through which the rod of the plunger extends therethrough;
      (iii) biasing means positioned between the piston and the first end of the housing, the biasing means biasing the piston toward the second end of the housing;
      (iv) ratchet means which engage the piston with the rod of the plunger when the biasing means is overcome and the piston is urged toward the first end of the housing, the plunger being indexed toward the first end of the syringe a distance which corresponds to the predetermined distance which the piston travels, and wherein the indexed distance which the plunger travels corresponds to a precise volume of fluidic material.

2. The device of claim 1 wherein a pressure chamber is formed in the bore between the piston and the end plate, and further wherein the introduction of fluid into the pressure chamber provides a force to overcome the biasing means and urges the piston toward the first end of the housing.

3. The device of claim 2 wherein the end plate further includes a port through which the fluid may be introduced.

4. The device of claim 2 wherein the fluid is compressed air.

5. The device of claim 2 further including a means for pulsing the introduction of fluid into the pressure chamber, each pulse indexing the plunger toward the first end of the syringe a distance which corresponds to the predetermined distance which the piston travels and wherein the volume of fluidic material forced from the hollow barrel corresponds to the number of pulses produced by the means for pulsing.

6. The device of claim 1 wherein the bore has a first diametral dimension, a second diametral dimension which is less than the first diametral dimension, and a ledge formed at the interface between the first diametral dimension and the second diametral dimension, the piston abutting against the ledge upon travel of the piston toward the first end of the housing to define an end point of the predetermined distance which the piston travels.

7. The device of claim 1 wherein the ratchet means comprises teeth along the rod which is attached to the plunger and a leaf spring which engages the teeth.

8. The device of claim 7 wherein the leaf spring is located intermediate the piston and the means for biasing.

9. The device of claim 7 wherein the leaf spring is located intermediate the second end of the syringe and the first end of the housing.

10. A device for injection of fluidic materials into body tissue, the device comprising:
(a) a syringe having a first end, a second end that opposes the first end, and a hollow barrel which is oriented along a longitudinal axis of the syringe, the syringe including a plunger which travels within the hollow barrel such that travel of the plunger toward the first end forces the fluidic material from the hollow barrel and travel of the plunger toward the second end draws the fluidic material into the hollow barrel, and the syringe further including a rod which is attached to the plunger and which extends beyond the second end of the syringe;
(b) a housing having a first end, a second end that opposes the first end of the housing, and a bore which is oriented along a longitudinal axis of the housing, the first end of the housing being in juxtaposed relationship with the second end of the syringe, and wherein the longitudinal axis of the housing and the longitudinal axis of the syringe are the same such that the bore of the housing and the barrel of the syringe are in concentric relationship, the housing further comprising:
(i) an end plate which is located at the second end of the housing, the end plate having an aperture through which the rod of the plunger extends beyond the second end of the housing and a port through which fluid may be introduced;
(ii) a piston which travels a predetermined distance within the bore of the housing, the piston having a hole concentric with the longitudinal axis through which the rod of the plunger extends therethrough, wherein a pressure chamber is formed in the bore between the piston and the plate, the pressure chamber being in fluid communication with the port;
(iii) biasing means positioned between the piston and the first end of the housing, the biasing means biasing the piston toward the second end of the housing;
(iv) ratchet means which engage the piston with the rod of the plunger when the biasing means is overcome and the piston is urged toward the first end of the housing, the plunger being indexed toward the first end of the syringe a distance which corresponds to the predetermined distance which the piston travels, and wherein the indexed distance which the plunger travels corresponds to a precise volume of fluidic material, wherein the bore has a first diametral dimension, a second diametral dimension which is less than the first diametral dimension, and a ledge formed at the interface between the first diametral dimension and the second diametral dimension, the piston abutting against the ledge upon travel of the piston toward the first end of the housing to define an end point of the predetermined distance which the piston travels and further wherein the ratchet means comprises teeth along the rod which is attached to the plunger and a leaf spring which engages the teeth.

11. The device of claim 10 wherein the fluid is compressed air.

12. The device of claim 10 further including a means for pulsing the introduction of fluid into the pressure chamber, each pulse indexing the plunger toward the first end of the syringe a distance which corresponds to the predetermined distance which the piston travels and wherein the volume of fluidic material forced from the hollow barrel corresponds to the number of pulses produced by the means for pulsing.

13. The device of claim 10 wherein the leaf spring is located intermediate the piston and the means for biasing.

14. The device of claim 10 wherein the leaf spring is located intermediate the second end of the syringe and the first end of the housing.

15. A device for injection of fluidic materials into body tissue, the device comprising:
(a) a syringe having a first end, a second end that opposes the first end, and a hollow barrel which is oriented along a longitudinal axis of the syringe, the syringe including a plunger which travels within the hollow barrel such that travel of the plunger toward the first end forces the fluidic material from the hollow barrel and travel of the plunger toward the second end draws the fluidic material into the hollow barrel, and wherein the syringe further includes a rod which is mounted on the plunger and which extends beyond the second end of the syringe;
(b) a housing having a first end, a second end that opposes the first end of the housing, and a bore, and wherein a pressure chamber is formed in the bore between the piston and the second end of the housing, and further wherein the introduction of a pulse of fluid from a pneumatic source into the pressure chamber provides a force which urges the piston toward the first end of the housing;
(c) a biasing assembly positioned to bias the plunger towards the second end of the syringe;

(d) a ratchet assembly which couples the piston with the road when the biasing means is overcome and the piston is urged toward the first end of the housing, and wherein the plunger is indexed toward the first end of the syringe a distance which corresponds to the predetermined distance which the piston travels, and wherein the indexed distance which the plunger travels corresponds to a precise volume of fluidic material; and (e) a means for pulsing disposed in fluid communication with the pressure chamber, and wherein the pulsing means introduces fluid into the pressure chamber, and wherein each pulse indexes the plunger toward the first end of the syringe a distance which corresponds to the predetermined distance which the piston travels, and wherein the volume of fluidic material forced from the hollow barrel corresponds to the number of pluses produced by the pulsing means.

* * * * *

UNITED STATES PATENT AND TRADEMARK OFFICE
CERTIFICATE OF CORRECTION

PATENT NO. : 5,370,630
DATED : December 6, 1994
INVENTOR(S) : Michael J. Smidebush, et al It is certified that error appears in the above-indentified patent and that said Letters Patent is hereby corrected as shown below:

Col. 2, line 63, delete the word "volume:" and insert -- volume --.

Col. 5, line 59, delete the word "frown" and insert -- from --.

Signed and Sealed this

Twenty-eight Day of February, 1995

*Attest:*

BRUCE LEHMAN

*Attesting Officer*     *Commissioner of Patents and Trademarks*